(12) United States Patent
Poponin

(10) Patent No.: US 6,376,177 B1
(45) Date of Patent: Apr. 23, 2002

(54) APPARATUS AND METHOD FOR THE ANALYSIS OF NUCLEIC ACIDS HYBRIDIZATION ON HIGH DENSITY NA CHIPS

(75) Inventor: Vladimir Poponin, San Francisco, CA (US)

(73) Assignee: Virtual Pro, Inc., San Francisco, CA (US)

( * ) Notice: Subject to any disclaimer, the term of this patent is extended or adjusted under 35 U.S.C. 154(b) by 0 days.

(21) Appl. No.: 09/413,596

(22) Filed: Oct. 6, 1999

(51) Int. Cl.$^7$ ................................................ C12Q 1/68
(52) U.S. Cl. .............................. 435/6; 536/243; 436/2
(58) Field of Search .............................. 435/6; 536/24.3

(56) References Cited

U.S. PATENT DOCUMENTS

| | | |
|---|---|---|
| 5,244,636 A | 9/1993 | Walt et al. |
| 5,629,213 A * | 5/1997 | Kornguth et al. ........... 436/518 |
| 5,695,940 A | 12/1997 | Drmanac et al. |
| 5,814,516 A | 9/1998 | Vo-Dinh |
| 5,821,060 A | 10/1998 | Arlinghaus et al. |
| 5,866,330 A | 2/1999 | Kinzler et al. |
| 5,871,628 A | 2/1999 | Dabiri et al. |
| 5,874,219 A | 2/1999 | Rava et al. |
| 5,908,745 A | 6/1999 | Mirzabekov et al. |
| 5,919,626 A | 7/1999 | Shi et al. |
| 5,928,862 A | 7/1999 | Morrison |
| 5,932,711 A | 8/1999 | Boles et al. |
| 5,952,174 A | 9/1999 | Nikiforov et al. |

OTHER PUBLICATIONS

Deckert et al., "Near–Field Surface Enhanced Raman Imaging of Dye–Labeled DNA with 100–nm Resolution" Analytical Chemistry vol. 70, pp. 2646–2650, 1998.*

Chumanov et al. "Surface Enhanced Raman Scattering for Discovering and Scoring Single Base Differences in DNA." Proceedings SPIE. (1999) vol. 3608.

Kneipp et al. "Surface Enhanced Raman Spectroscopy on Nucleic Acids and Related Compounds Adsorbed on Colloidal Silver Particles." *Journal of Molecular Structure.* (1991) 244: 183–192.

Kneipp et al. "Single Molecule Detection Using Surface–Enhanced Raman Scattering (SERS)." *The American Physical Society.* (Mar. 3, 1997) 78(9).

Vo–Dinh et al. "Surface–Enhanced Raman Gene Probes." *Anal. Chem.* (1994) 66: 3379–3383.

Emory et al. "Near–Field Surface–Enhanced Raman Spectroscopy on Single Silver Nanoparticles." *Anal. Chem.* (1997) 69: 2631–2635.

Cotton et al. "Application of Surface–Enhanced Raman Spectoscopy to Biological Systems" *Journal of Raman Spectroscopy.* (1991). 22: 729–742.

Guschin et al. "Manual Manufacturing of Oligonucleotide, DNA, and Protein Microchips[1]." *Analytical Biochemistry.* (1997). 250: 203–211.

Bauer et al. "Optical Nanocluster Microchips for Human Diagnostics." Institut fur Biochemie und Molekulare Zellbiologie und Ludwig Bolzmann–Forschungsstelle fur Biochemie, Universitat Wien.

Bauer et al. "Microarray based optical biochip with nanometric resolution." Institut fur Biochemie und Molekulare Zellbiologie, Universitat Wien.

Thomas, George J., Jr "Raman Spectroscopy of Protein and Nucleic Acid Assemblies." *Annu. Rev. Biophys Biomol. Struct.* (1999) 28: 1–27.

Bej, Asim K., "Nucleic Acid Hybridizations: Principles and Strategies." *Nucleic Acid Analysis: Principles and Bioapplications.* (1996) 1–29.

Adams, M.D. "Expressed Sequence Tags as Tools for Physiology and Genomics." *The Institute for Genomic Research.* Chapter 10: 71–76.

Martin–Gallardo, et al. "Shotgun Sequencing." Human Genome Center, Biology and Biotechnology Program, Lawrence Livermore National Laboratory. Chapter 5: 37–41.

Dramanc, et al. "Sequencing by Hybridization." Integral Genetics Group, Biological and Medical Research Division, Argonne National Laboratory. Chapter 4: 29–36 .

* cited by examiner

*Primary Examiner*—John S. Brusca
*Assistant Examiner*—Jeffrey S. Lundgren
(74) *Attorney, Agent, or Firm*—William A. Barrett; Steven J. Hultquist

(57) ABSTRACT

The invention generally relates to a new gene probe biosensor employing near field surface enhanced Raman scattering (NFSERS) for direct spectroscopic detection of hybridized molecules (such as hybridized DNA) without the need for labels, and the invention also relates to methods for using the biosensor.

10 Claims, 4 Drawing Sheets

APPARATUS AND METHOD FOR THE ANALYSIS OF NUCLEIC ACIDS HYBRIDIZATION ON HIGH DENSITY NA CHIPS

TABLE OF CONTENTS . . .
TABLE OF CONTENTS . . .
  1. FIELD OF THE INVENTION . . .
    1.1 BRIEF DESCRIPTION OF THE INVENTION . .
    1.2 BACKGROUND OF THE INVENTION . . .
  2. SUMMARY OF THE INVENTION . . .
  3. BRIEF DESCRIPTION OF THE DRAWINGS . . .
  4. DETAILED DESCRIPTION OF THE INVENTION . . .
  5. EXAMPLES . . .
  6. REFERENCES . . .
THE CLAIMS . . .
ABSTRACT . . .

1. FIELD OF THE INVENTION

1.1 Brief Description of the Invention

The invention disclosed herein relates to a new gene probe biosensor employing near field surface enhanced Raman scattering (NFSERS) for direct spectroscopic detection of DNA hybridization without the need for labels, and the invention also relates to methods for using the biosensor.

1.2 Background of the Invention

In 1928, C. V. Raman and his collaborator, K. S. Krishnan, established that the spectrum of inelastically scattered light can provide a unique fingerprint of molecular structure. Since this initial discovery, Raman spectroscopy has advanced dramatically. Many Raman-related analytical instruments have been developed, some of which have applicability to proteins and nucleic acids. Recent developments have enabled the use of Raman spectroscopy to obtain information such as conformation and/or orientation of molecules and some molecular groups, local hydrogen bonding interactions, and time dependence of structural or organizational properties. Thomas, G. J., "Raman Spectroscopy of Protein and Nucleic Acid Assemblies," *Annu. Rev. Biophys. Biomol. Struct.* 28:1–27 (1999).

The discrete vibrational energies (Raman band frequencies), scattering probabilities (Raman intensities) and tensor characteristics (Raman polarizations) that constitute the Raman spectra are a function of molecular geometry and intra- and intermolecular force fields.

Early experimental work in the field of Raman spectroscopy demonstrated the advantages of surface-enhanced Raman scattering (SERS) as a technique for detecting and identifying molecules. See Cotton, T. M. "Application of Surface-Enhanced Raman Spectroscopy to Biological Systems" *J. Raman Spect.* 23: 729–742 (1991). For example, between 1974 and 1977, several researchers showed that Raman scattering from pyridine on a roughened silver electrode was enhanced by approximately six orders of magnitude. Id. SERS has been used to study various types of amino acids and peptides on silver surfaces, as well as to study the behavior of DNA at silver colloids.

Surface enhanced Raman scattering has also been investigated as a method for detecting and identifying single base differences in double stranded DNA fragments. Chumanov, G. "Surface Enhanced Raman Scattering for Discovering and Scoring Single Based Differences in DNA" Proc. Volume *SPIE*, 3608 (1999).

SERS has also been used for single molecule detection. Kneipp, K. "Single Molecule Detection Using Surface-Enhanced Raman Scattering (SERS)" Physical Review Letters 78(9):1667–1670 (1997). SERS results in strongly increased Raman signals from molecules which have been attached to nanometer sized metallic structures.

SERS principles have also been used in the development of gene probes which do not require the use of radioactive labels. These probes can be used to detect DNA via hybridization to a DNA sequence complementary to the probe. Vo-Dinh, T. "Surface-Enhanced Raman Gene Probes" *Anal. Chem.* 66:3379–3383 (1994).

The Human Genome Project and other recent advances in molecular biology have spurred the development of new methods for the labeling and detection of DNA and DNA fragments.

Traditionally, radioisotopes have been used as labels for DNA. More recently, fluorescent, chemiluminescent and bioactive reporter groups have been used. The reporter groups are typically incorporated in the primers or the deoxynucleoside triphosphates to label the newly synthesized DNA fragments. The DNA fragments of interest are allowed to hybridize to a set of bound or immobilized DNA fragments.

Among the various methods for identifying genes, the most widely used are technologies which require radioactive labels. A variety of disadvantages are associated with the use of radioactive labels, including the short shelf life of common labels and the safety hazards associated with the use of radioactive compounds. Accordingly, there is a strong need in the art for a method for identifying genes which does not require the use of radioactive labels.

Methods for manufacturing oligonucleotide, DNA and protein microchips and microarrays are known in the art. Research is ongoing into the use of such microchips and microarrays in DNA and RNA sequence analysis, diagnostics of genetic disease, gene polymorphisms studies, and analysis of gene expression. Microchips have been developed in which oligonucleotides are immobilized within polyacrylamide gel pads. Robotics can be employed for the manufacture of microchips containing thousands of immobilized compounds.

Various attempts have been made to enable the sequencing of DNA without the necessity of using radioisotopes, or fluorescent substances. For example, U.S. Pat. No. 5,821,060 describes a process for DNA sequencing, mapping and diagnostics which utilizes the differences between the chemical composition of DNA and that of peptide nucleic acid sequences (PNAs) to provide DNA sequencing, mapping or diagnostics using natural DNA fragments. The process includes the steps of hybridizing PNA segments to complementary DNA segments which are affixed to a hybridization surface, or hybridizing in DNA segments to complementary PNA segments which are fixed to a hybridization surface and using mass spectrometric or non-mass spectrometric techniques to analyze the extent of hybridization at each potential hybridization site.

It is a an object of the present invention to provide molecular sequencing, mapping, screening, diagnostic process and other molecular hybridization processes, in which normal, unlabled DNA is used rather than DNA labeled with stable isotopes, radioactive isotopes or fluorescent groups, and which provides superior spectral specificity as compared to methods of the prior art. Achieving this object will eliminate some of the expensive reagents and labor involved in the labeling of DNA and thereby significantly reduce time, effort and expense of DNA analysis, while enabling highly accurate DNA sequencing, mapping, screening, diagnostic and other molecular hybridization related processes.

In some cases, polymorphisms comprise mutations that are the determinantive characteristic in a genetic disease (hemophilia, sickle-cell anemia, etc.). A "polymorphism" is a variation in the DNA sequence of some members of a species. A polymorphism is said to be "allelic" because some members of a species have the mutated sequence, while other members have the non-mutated sequence. Single nucleotide polymorphisms (SNPs) contain a polymorphic site. A variety of methods have been developed for the characterization of SNPs. Such methods include, for example, the direct or indirect sequencing of the site, the use of restriction enzymes with specificity for the allelic site to create or destroy a restriction site, the use of allele-specific hybridization probes, the use of antibodies that are specific for the proteins encoded by the different alleles of the polymorphism, and other biochemical techniques. It is an object of the present invention to provide advanced surface detection methods which enable the characterization of SNPs without the necessity for the use of restriction enzymes which affect the SNP site, without the necessity for allele-specific hybridization probes, and without the necessity of using antibodies specific for the proteins encoded by the different alleles of the polymorphism.

Other objects and advantages of the present invention over the prior art will become apparent to those skilled in the art upon review of the detailed description that follows.

2. SUMMARY OF THE INVENTION

The applicant has surprisingly and unexpectedly discovered, using a novel analytic technique, coupling near-field optics with SERS techniques, that each hybridization member in a hybridized pair of molecules (e.g., hybridized DNA fragments) has a unique spectrum of low frequency (lattice-type) vibrations. The novel analytic technique presented herein is employed in the novel spectroscopic instrument of the present invention, which is useful for detecting molecular hybridization. The novel instrument and methods presented herein enable vastly improved spectral sensitivity as compared to known methods.

One object of the present invention is to provide a more efficient, reliable, faster and more accurate method for direct detection of nucleic acid hybridization on high density nucleic acid chips. The invention provides direct spectroscopic detection of DNA—DNA, DNA—RNA, and RNA—RNA hybridization.

Among the many advantages of the apparatus and method of the present invention, are the ability to eliminate the need for labeling (by fluorescent or other labels) as is required in currently used methods. Furthermore, the apparatus and method of the present invention enable high throughput screening of DNA without the necessity for PCR amplification.

The invention provides an analytical method for determining whether a DNA sample comprises double-stranded DNA, said method comprising analyzing the DNA sample by near field Raman spectroscopy to determine whether the sample produces lattice vibrations, wherein the presence of lattice vibrations indicates the presence of double stranded DNA in the DNA sample. In a preferred aspect, the DNA sample is associated with a substrate, e.g., a substrate selected from the group consisting of: nucleic acid chips, peptide nucleic acid chips, conducting carbon nanotube plates; microfluidic nucleic acid chips.

The invention also provides a spectroscopic system for detecting molecular hybridization, said system comprising a near-field SERS substrate arranged to support one or more predetermined hybridizeable molecules thereon; a coherent radiation source arranged to impinge coherent radiation onto each of the hybridizeable molecules to responsively produce a pattern of scattered photons; a photonic collector arranged in photon-gathering relationship to the scattered photons and adapted to transmit the gathered scattered photons; a Raman spectrograph arranged in photon receiving relationship to the photonic collector and adapted to generate an output correlative to the collected scattered photons transmitted by the photonic collector; and a spectral to electronic converter, arranged to receive the output of the Raman spectrograph and to convert same to an electronic output indicative of the presence or absence of hybridized molecules on the SERS substrate.

In another embodiment, the near field SERS substrate is selected from the group consisting of: nucleic acid chips, peptide nucleic acid chips, conducting carbon nanotube plates, microfluidic nucleic acid chips, optical nanocluster microchips, plates coated with colloid silver, plates coated with colloid gold, plates coated with colloid platinum, and conducting carbon nanotube plates. The near field SERS substrate is a preferably a microchip or microarray.

The one or more predetermined hybridizeable molecules disposed on the near field SERS substrate are preferably ssDNA or ssRNA.

The laser light source is preferably selected from the group consisting of: argon ion lasers, infrared lasers, and ultraviolet lasers.

The spectral to electronic converter preferably comprises a CCD array and the photonic collector optionally comprises an ICCD array.

The present invention also provides a method for detecting hybridized DNA comprising providing the spectroscopic system described above; exposing the predetermined hybridizeable molecules disposed on the near field SERS substrate to a sample containing one or more sample molecules having the capacity to hybridize to the predetermined hybridizeable molecules; directing the laser beam from the laser light source onto each of the one or more predetermined hybridizeable molecules to create a pattern of scattered photons for each of said hybridizeable molecules; collecting the scattered photons for each of said hybridizeable molecules and directing them to a Raman spectrograph; collecting photonic data from the Raman spectrograph and transforming said photonic data into electronic data for further data processing; and determining whether each of the hybridizeable molecule is hybridized to a sample molecule by comparing the Raman spectrum of (i) each hybridizeable molecule exposed to the sample to (ii) the Raman spectrum to the corresponding unhybridized predetermined hybridizeable molecule.

Other aspects of the invention will become apparent to those of skill in the art from the drawings of FIGS. 1–4 and the Brief Description of the Drawings presented in Section 3 hereof, from the Detailed Description of the Invention in Section 4 hereof, and from the Examples, presented in Section 5 hereof.

3. BRIEF DESCRIPTION OF THE DRAWINGS

4. DETAILED DESCRIPTION OF THE INVENTION

Figure 1:
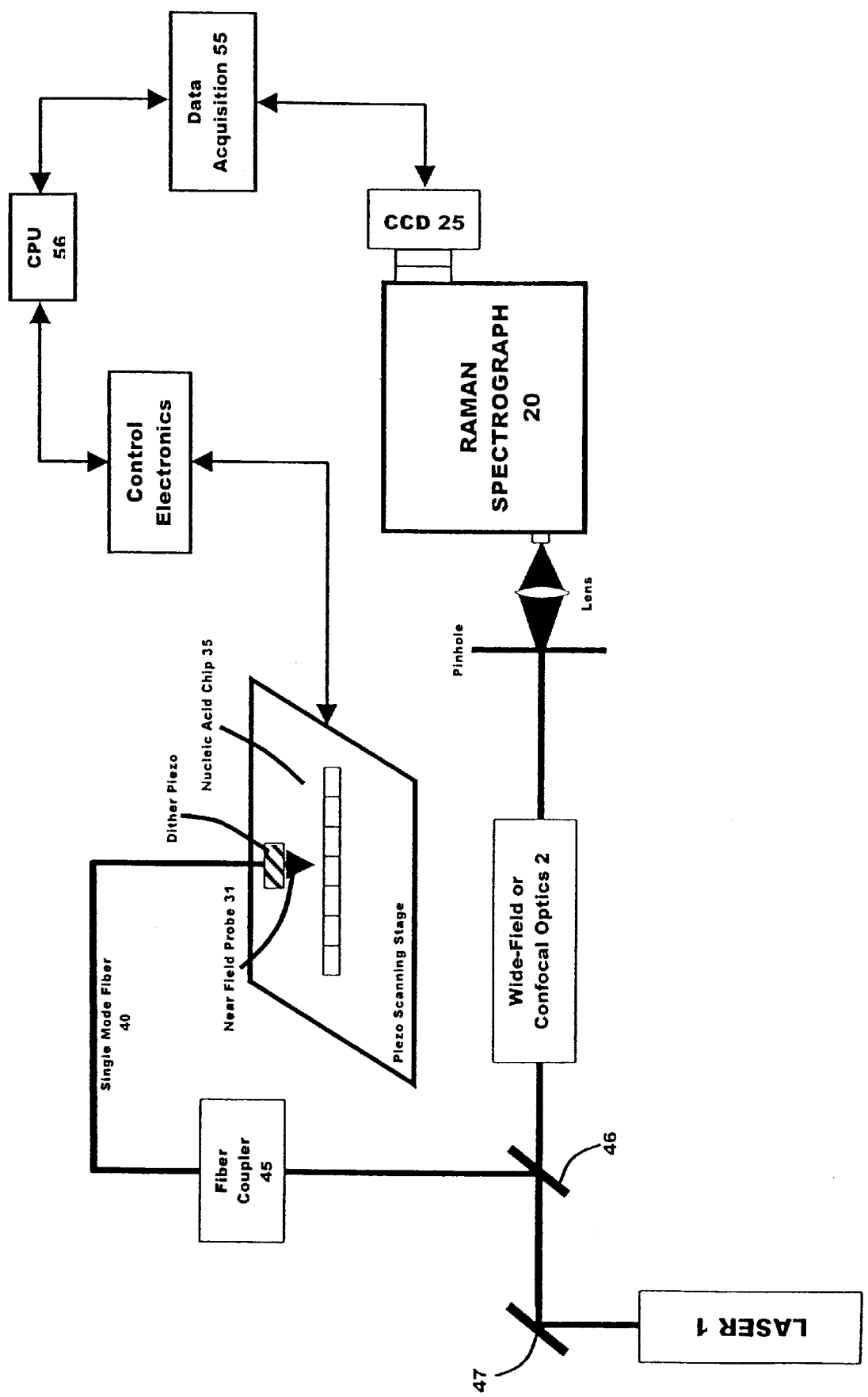
FIG. 1 is a schematic diagram of a near field SERS gene detection system of the present invention.

The applicant has surprisingly and unexpectedly discovered, using a novel analytic technique, coupling near-field optics with SERS techniques, that each hybridization member in a hybridized pair of molecules (e.g., hybridized DNA fragments) has a unique spectrum of low frequency (lattice-type) vibrations and that this unique spectral "fingerprint" may be used for highly effective characterization of hybridizeable molecules. For example, the data presented herein indicates that since dsDNA is similar to a crystal structure, each hybridization member has a unique spectral feature of low frequency (lattice type) vibrations of 0–300 $cm^{-1}$ spectral interval.

The novel analytic technique presented herein enables the construction of a novel spectroscopic instrument for detecting molecular hybridization. Coupling of near-field optics with SERS techniques enables sub-wavelength (e.g., 50 nm) nm-scale spatial resolution. This magnitude of spatial resolution results in a degree of sensitivity which is 3 orders of magnitude higher than the sensitivity of standard luminescent probes (see Kniepp, K., "Surface-Enhanced Raman Spectroscopy on Nucleic Acids and Related Compounds Adsorbed on Colloidal Silver Particles," *J. Molecular Structure* 244:183–192 (1991); Kniepp, K., "Single Molecule Detection Using Surface-Enhanced Raman Scattering (SERS)," *Physical Review Letters* 78(9) 1667–1670 (1997)) and permits the use of laser light having an extremely low intensity of excitation (~10 nW).

The novel instrument and methods presented herein enable vastly improved spectral sensitivity as compared to known methods. The combination of near-field optics and SERS techniques enables the use of multi-mode fiber probes for reading of hybridization patterns and spectral fingerprints. Up to 2000 channels can be employed in one fiber bundle. Data transmitted by the fiber bundle can be transmitted to a CCD array detector for translation into computer-readable data for transmission to a CPU. The general scheme of an instrument according to this embodiment of the present invention is set forth in FIG. 1.

Types of Raman spectroscopy useful according to the present invention include, for example, resonance Raman spectroscopy (RRS), surface enhanced Raman spectroscopy (SERS), surface enhanced resonance Raman spectroscopy (SERRS), and laser induced fluorescence (LIF) and luminescence. The preferred type is SERS.

The biosensor instrument of the present invention generally comprises a support structure, a near field SERS gene probe having at least one predetermined oligonucleotide strand and an SERS active substrate disposed on the support structure and having at least one of the near field SERS gene probes adsorbed thereon. Biotargets, such as bacterial and viral DNA, RNA and PNA are detected using a near field SER gene probe via hybridization to oligonucleotide strands complimentary to the near field SER gene probe. The SERS active substrate, in one embodiment, includes a fiberoptic probe, an array of fiberoptic probes for performance of multiple assays and preferably includes a waveguide microsensor array with charge-coupled devices (CCD) or photodiode arrays.

Referring now to FIG. 1, a nucleic acid chip comprising a SERS active substrate is disposed on a piezo scanning stage. A near field probe is supplied with a dither piezo. In this embodiment, 50 nm spatial resolutions can be achieved; however, the speed of recording information will be slow, i.e., in the range of several minutes per sample. Other motion stage arrangements can be alternatively utilized. In the arrangement of FIG. 1, the laser 1 (e.g., an argon ion laser) generates continuous wave (CW) coherent radiation with power in range up to 25 mWt with wavelength 514.5 nm (or 488 nm). The mirror 47 directs a light beam onto a light splitter prism 46. In the fiber coupler 45, the incident light beam is transformed into a single or multi-mode optical fiber 40. The intensity of light in each individual fiber is substantially attenuated (up to 10 nWt level). The light beam then impinges upon the hybridizeable molecule (e.g., the DNA oligonucleotide on the SERS active substrate) through the near field probe 31. The probe focuses incident radiation on an area with size as small as about 50 nm. The size of a pixel on the DNA chip should be no smaller than the focusing area of the incident light, i.e., in a range from about 50 nm to about 20 microns. At the pixel of the nucleic acid chip 35, incident laser light is interacting with the vibrational modes of the DNA fragments to produce scattered light via a surface enhanced Raman scattering process. Backscattered radiation is collected by the near field probe 31 and propagates backward along a corresponding optical fiber. After passing through the fiber coupler 45 and splitter 46 scattered radiation is delivered by wide field or collimated optics 2 to the Raman spectrograph 20. In the Raman spectrograph 20, scattered light is analyzed and transformed into digital form by a CCD array 25. Digital data are delivered through the data acquisition system 55 (which separates and synchronizes different time segments and provides preliminary processing and filtration of data) into the CPU 56 for further processing.

The probe DNA oligonucleotides are placed on the SERS active substrate. Reflection-back-to-the fiber-mode of operation of the scanning near field optical microscope (NOM) is preferred.

It should be noted that the method of the present invention can also operated in a site addressable manner.

In an alternative embodiment, the nucleic acid chip on the SERS active substrate can be placed on an optical disk support (similar to CD-ROM or DVD-ROM). In this embodiment, the near field probe is immovable and scanning of the nucleic acid chip is accomplished by the motion of the nucleic acid optical disk in a CD/DVD-ROM device. In this embodiment, spatial resolution will be about 20 microns per pixel (the same as in currently commercially available DNA chip technology and optical chip readers based on luminescence detection from luminescence labels); however, the speed at which the nucleic acid chip can be read will be in the range of microseconds to milliseconds.

In a third embodiment, random array technology may be used in combination with a fiber optic sensor (e.g., a sensor arrangement of the type disclosed in U.S. Pat. Nos. 5,244,636 and 5,244,813). In this embodiment, ultimate spatial resolution is 5 microns per pixel, enabling the speed at which the chip can be read to be reduced to microseconds.

Optical IR fiber employed in the practice of the present invention may be single-mode fiber or a multi-mode fiber bundle. Multi-mode fiber bundles, which commonly have up to 2000 fibers in one bundle, may be used in multichannel recording.

A fiber coupler may be used to transfer illuminating and scattered optical signals into large aperture beams and vice versa. A splitter can be used to send reflected light through wide-field or confocal optics into the Raman spectrograph.

The preferred source of illuminating radiation is an argon ion laser, although other suitable radiation sources may be usefully employed in the general practice of the invention. The laser beam may be directed into the system using a mirror arrangement.

A CCD array detector can be used to transform spectral information into digital information for transmission to data storage and/or to a CPU for further processing. The data storage and/or CPU may be components of a standard personal computer or workstation for high-speed analyses of hyperspectral Raman imaging data arrays.

Where the SNOM is employed (first embodiment above), a signal from the piezo scanning device 30 is transferred to the control electronics system.

The spectral range of Raman spectra used in the near field SERS molecular hybridization detection system of the present invention is preferably in the range of about 0 to about 1700 $sm^{-1}$ with the preferred spectral interval ranging from about 0 to about 300 $sm^{-1}$. It is anticipated that the best results will be in a spectral interval which ranges from 10 to about 150 $sm^{-1}$.

The present invention also provides a method for detecting hybridization of molecules using the near field SERS technology of the present invention. The method is enabled by the fundamental property that single stranded and double stranded fragments of nucleic acids have different characteristic frequencies in Raman spectra. In fact, each complimentary fragment of DNA from a set of double stranded DNA fragments has an intrinsic low frequency vibrational spectra. As a general example, the frequency range varies from about 1 $cm^{-1}$ to about 4000 $cm^{-1}$, and the preferred range is from about 1 $cm^{-1}$ and about 400 $cm^{-1}$.

Each specific nucleic acid sequence will have a specific pattern of characteristic frequencies. A device analogous to a Raman microscope can be used to identify the chips containing hundreds of thousands of genes up to and including the entire human genome.

Scanning and multichannel CCD detection make the process very fast, and subsequent computer analysis can provide necessary data and information, for example, the differential gene expression, serial analysis of gene expression i.e., SAGE, and single nucleotide polymorphisms.

In addition to ordinary nucleic acid chips, other chips useful the practice of the present invention include, for example, peptide nucleic acid chips (PNA). PNA chips typically contain a layer of metal, preferably gold, platinum or silver. Plates from conducting carbon nanotubes are also useful in the apparatus and method of the present invention. The substrate may also be a microfluidic nucleic acid chip, such as a microfluidic DNA chip.

It will be understood by those of skill in the art that the present invention is useful for high-speed high-throughput analyses of genetic materials, such as the human genome.

5. EXAMPLES

The SPEX Triple Mate™ system was used to generate far field Raman spectra from DNA components. An ion argon laser with 514.5 nm wavelength was used for excitation of Raman spectra. The ion argon laser provided continuous wave power at 25 mWt. A triple-grating spectrometer was equipped with photomultiplier tube, operated in a single-photon counting mode. right-angle geometry of the laser excitation source and the scattering radiation was employed.

Figure 2:
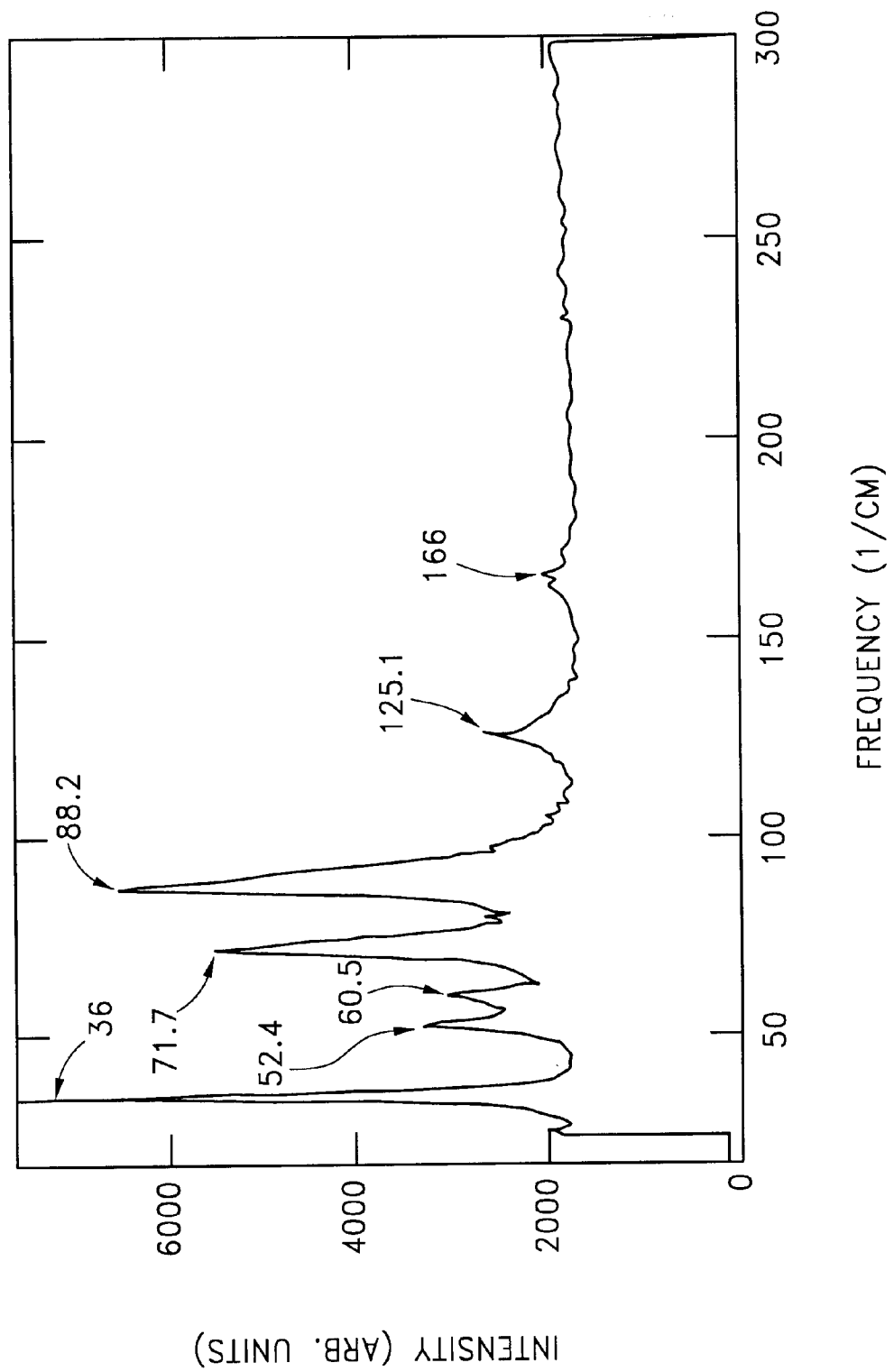
FIG. 2 shows a Raman spectrum of adenine (one of the major base constituents of DNA) in polycrystalline form obtained by using SPEX Triple Mate Raman spectrometer.

FIG. 2 shows Raman spectra of adenine (one of the major base constituents of DNA) in polycrystalline form obtained by using SPEX Triple Mate™ Raman spectrometer. An ion argon laser with 514.5 nm wavelength was used for excitation of Raman spectra. The ion argon laser provided continuous wave power at 25 mWt. A triple-grating spectrometer was equipped with photomultiplier tube, operated in a single-photon counting mode. The spectrum demonstrates several sharp vibrational lines in a range 10–200 $cm^{-1}$. These lines correspond to lattice vibrations and may be observed only in crystalline or quasicrystalline structures. An example of such a structure is double stranded DNA, which appears in hybridization procedures.

Figure 3:
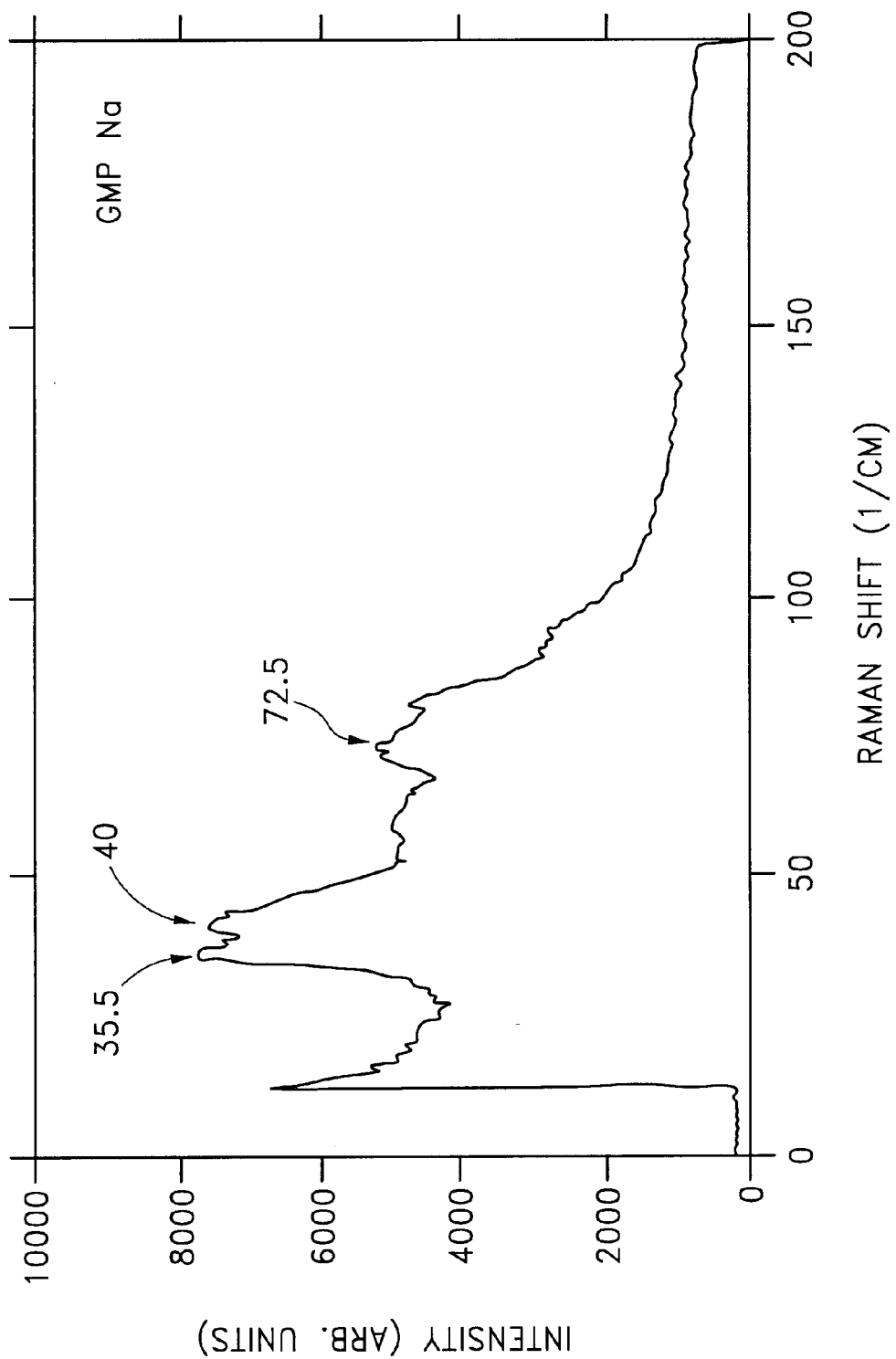
FIG. 3 shows a low frequency Raman spectrum, for polycrystalline guanosine monophosphate GMP Na.

FIG. 3 shows low frequency Raman spectra for polycrystalline guanosine monophosphate GMP Na. The experimental conditions are the same as those described above for adenine. Again the spectra demonstrate low frequency vibrational modes which are less sharp than in case of adenine.

Figure 4:
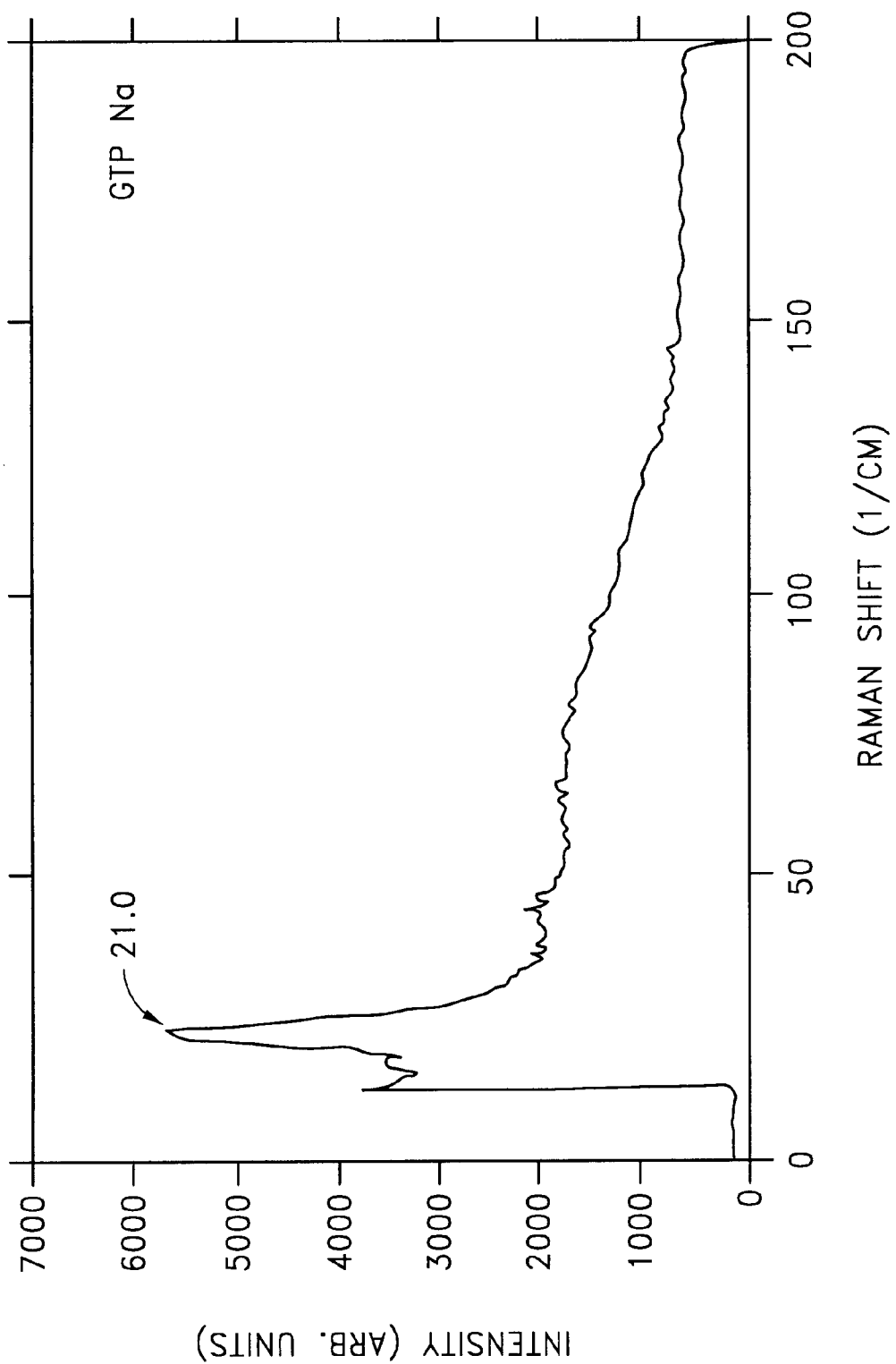
FIG. 4 shows a low frequency Raman spectrum for polycrystalline guanosine triphosphate GTP Na.

FIG. 4 shows a low frequency Raman spectra for polycrystalline guanosine triphosphate GTP Na. Experimental conditions are the same as in previous figures. Again spectra demonstrate at least one sharp low frequency vibrational line 21.0 $cm^{-1}$.

6. REFERENCES

Throughout this specification, various patent and non-patent references have been cited. The entire disclosure of each of these references is incorporated herein by reference, as is the entire disclosure of each of the following references:

Bauer et al. "Microarray Based Optical Biochip with Nanometric Resolution."

Bauer et al. "Optical Nanocluster Microchips for Human Diagnostics."

Chumanov et al. "Surface Enhanced Raman Scattering for Discovering and Scoring Single Base Differences in DNA." Proceedings *SPIE*, Vol. 3608, 1999.

Cotton et al. "Application of Surface-Enhanced Raman Spectroscopy to Biological Systems." *Journal of Raman spectroscopy*, Vol. 22, 729–742 (1991).

Emory et al. "Near-Field Surface-Enhanced Raman Spectroscopy on Single Silver Nanoparticles." *Anal. Chem.* Jul. 15, 1997, Vol. 69 No. 14, pp. 2631–2635.

Guschin et al. "Manual Manufacturing of Oligonucleotide, DNA, and Protein Microchips." *Analytical Biochemistry,* 250, 203–211 (1997) Article No. AB972209.

Kneipp et al. "Single Molecule Detection Using Surface-Enhanced Raman Scattering (SERS)." *The American Physical Society Physical Review Letters*. Vol. 78, No. 9, pg. 1667.

Kneipp et al. "Surface Enhanced Raman Spectroscopy on Nucleic Acids and Related Compounds Adsorbed on Colloidal Silver Particles." *Journal of Molecular Structure*. 244 (1991) 183–192.

Vo-Dinh et al. "Surface-Enhanced Raman Gene Probes." *Anal. Chem.* 1994, 66, 3379–3383.

U.S. Pat. No. 5,244,636. Walt et al. "Imaging Fiber Optic Array Sensors, Apparatus, and Methods for Concurrently Detecting Multiple Analytes of Interest in a Fluid Sample." Sep. 14, 1993.

U.S. Pat. No. 5,695,940. Drmanac et al. "Method of Sequencing by Hybridization of Oligonucleotide Probes." Dec. 9, 1997.

U.S. Pat. No. 5,814,516. "Surface Enhanced Raman Gene Probe and Methods Thereof." Sep. 29, 1998.

U.S. Pat. No. 5,821,060. Arlinghaus et al. "DNA Sequencing, Mapping, and Diagnositc Processes Using Hybridization Chips and Unlabeled DNA." Oct. 13, 1998.

U.S. Pat. No. 5,866,330. Kinzler et al. "Method for Serial Analysis of Gene Expression." Feb. 2, 1999.

U.S. Pat. No. 5,871,628. Dabiri et al. "Automatic Sequencer/Genotyper Having Extended Spectral Response." Feb. 16, 1999.

U.S. Pat. No. 5,874,219. Rava et al. "Methods for Concurrently Processing Multiple Biological Chip Assays." Feb. 23, 1999.

U.S. Pat. No. 5,905,024. Mirzabekov et al. "Method for Performing Site-Specific Affinity Fractionation for Use in DNA Sequencing." May 18, 1999.

U.S. Pat. No. 5,908,745. Mirzabekov et al. "Use of Continuous/Contiguous Stacking Hybridization as a Diagnostic Tool." Jun. 1, 1999.

U.S. Pat. No. 5,919,626. Shi et al. "Attachment of Unmodified Nucleic Acids to Silanized Solid Phase Surfaces." Jul. 6, 1999.

U.S. Pat. No. 5,928,862. Morrison. "Competitive Homogeneous Assay." Jul. 27, 1999.

U.S. Pat. No. 5,932,711. Boles et al. "Nucleic Acid-Containing Polymerizable Complex." Aug. 3, 1999.

U.S. Pat. No. 5,952,174. Nikiforov et al. "Ligase/Polymerase-Mediated Genetic Bit Analysis of Single Nucleotide Polymorphisms and its use in Genetic Analysis." Sep. 14, 1999.

I claim:

1. An analytical method for determining whether an unlabeled DNA sample comprises double-stranded DNA, said method comprising analyzing the DNA sample associated with an SERS substrate by near field Raman spectroscopy to determine whether the sample produces lattice vibrations, wherein the presence of lattice vibrations indicates the presence of double stranded DNA in the DNA sample.

2. The method of claim 1 wherein the SERS substrate is selected from the group consisting of: nucleic acid chips, peptide nucleic acid chips, conducting carbon nanotube plates, and microfluidic nucleic acid assay.

3. A method for detecting hybridized unlabeled DNA or RNA, the method comprising:
 (a) providing a spectroscopic system for detecting molecular hybridization, said system comprising:
   (i) a near-field SERS substrate arrayed to support one or more unlabeled DNA or RNA samples thereon;
   (ii) a source of coherent radiation source arranged to impinge coherent radiation onto each of the unlabeled DNA or RNA samples to responsively produce a pattern of scattered photons;
   (iii) a photonic collector arranged in photon-gathering relationship to the photons and adapted to transmit the gathered scattered photons;
   (iv) a Raman spectrograph arranged in photon receiving relationship to the photonic collector and adapted to generate an output correlative to the collected scattered photons transmitted by the photonic collector; and
   (v) a spectral to electronic converter, arranged to receive the output of the Raman spectrograph and to convert to an electronic output indicative of the presence or absence of unlabeled DNA or RNA molecules on the SERS substrate;
 (b) exposing the unlabeled DNA or RNA molecules disposed on the near field SERS substrate to a sample containing one or more sample DNA or RNA molecules having the capacity to hybridize to the unlabeled DNA or RNA molecules;
 (c) directing the laser beam from the laser light source onto to create a pattern of scattered photons for each of said hybridizeable molecules;
 (d) collecting the scattered photons for each of said hybridizeable molecules and directing them to the Raman spectrograph;
 (e) collecting photonic data from the Raman spectrograph and transforming said photonic data into electronic data for further data processing; and
 (f) determining whether the unlabeled DNA or RNA has hybridized to the sample DNA or RNA moleculed by identifying the presence or absence of lattice vibrations wherein the presence of little vibrations is indicative of hybridization.

4. The method of claim 3 wherein the hybridizable molecule comprises DNA and wherein the determination of whether the hybridizeable molecule is hybridized to a sample molecule is indicated by the presence of lattice vibrations.

5. The method of claim 3 wherein the near field SERS substrate is selected from the group consisting of: nucleic acid chips, peptide nucleic acid chips, conducting carbon nanotube plates, microfluidic nucleic acid chips, and optical nanocluster microchips.

6. The method of claim 3 wherein the SERS substrate is selected from the group consisting of: plates coated with colloid silver, plates coated with colloid gold, plates coated with colloid platinum, and conducting carbon nanotube plates.

7. The method of claim 3 wherein the one or more predetermined hybridizeable molecules disposed on the near field SERS substrate are selected from the group consisting of: DNA, and RNA.

8. The method of claim 3 wherein the near field SERS substrate comprises a microchip or microarray.

9. The method of claim 3 wherein the laser light source is selected from the group consisting of: argon ion lasers, infrared lasers, and ultraviolet lasers.

10. The method of claim 3 wherein the spectral to electronic converter comprises a CCD array and/or wherein the photonic collector is an ICCD array.

* * * * *